United States Patent [19]

Lehtikoski et al.

[11] Patent Number: 4,596,152
[45] Date of Patent: Jun. 24, 1986

[54] METHOD OF MEASURING TEAR RESISTANCE OF PAPER AND APPARATUS FOR APPLYING THE METHOD

[76] Inventors: Olavi Lehtikoski, Sölvenkatu 8, SF-78300 Varkaus; Martti Nissinen, Kirvesniementie 2, SF-78880 Kuvansi, both of Finland

[21] Appl. No.: 653,248
[22] PCT Filed: Jan. 19, 1984
[86] PCT No.: PCT/FI84/00007
§ 371 Date: Sep. 7, 1984
§ 102(e) Date: Sep. 7, 1984
[87] PCT Pub. No.: WO84/02981
PCT Pub. Date: Aug. 2, 1984

[30] Foreign Application Priority Data
Jan. 19, 1983 [FI] Finland .................... 830176

[51] Int. Cl.⁴ ........................... G01N 3/08
[52] U.S. Cl. .................................. 73/835
[58] Field of Search ............... 73/835, 856, 159

[56] References Cited

U.S. PATENT DOCUMENTS

| | | | |
|---|---|---|---|
| 1,273,972 | 7/1918 | Wood | 73/835 |
| 1,423,842 | 7/1922 | Elmendorf | 73/835 |
| 1,447,185 | 3/1923 | Sammet | 73/835 |

FOREIGN PATENT DOCUMENTS

| | | |
|---|---|---|
| 33813 | 1/1922 | Norway . |
| 53472 | 4/1920 | Sweden . |

*Primary Examiner*—Anthony V. Ciarlante
*Attorney, Agent, or Firm*—Cohen, Pontani & Lieberman

[57] ABSTRACT

The invention relates to a method of measuring tear resistance of paper. At present, the measurements are effected by using a multi-layer pack of paper and by tearing it by means of the potential energy of a pendulum. According to the invention, a paper sample (1) is provided with a tongue-shaped test blank (2), whose one end (3) is secured to the paper sample, said paper sample is torn by pulling the test blank and/or paper sample in different directions relative to each other and the tearing force is measured.

13 Claims, 6 Drawing Figures

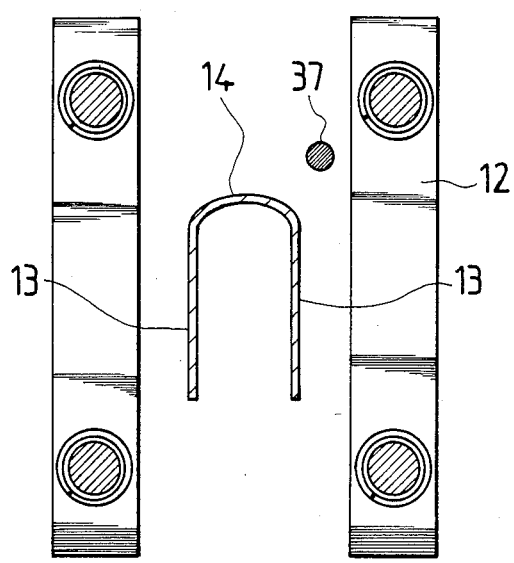
Fig. 2
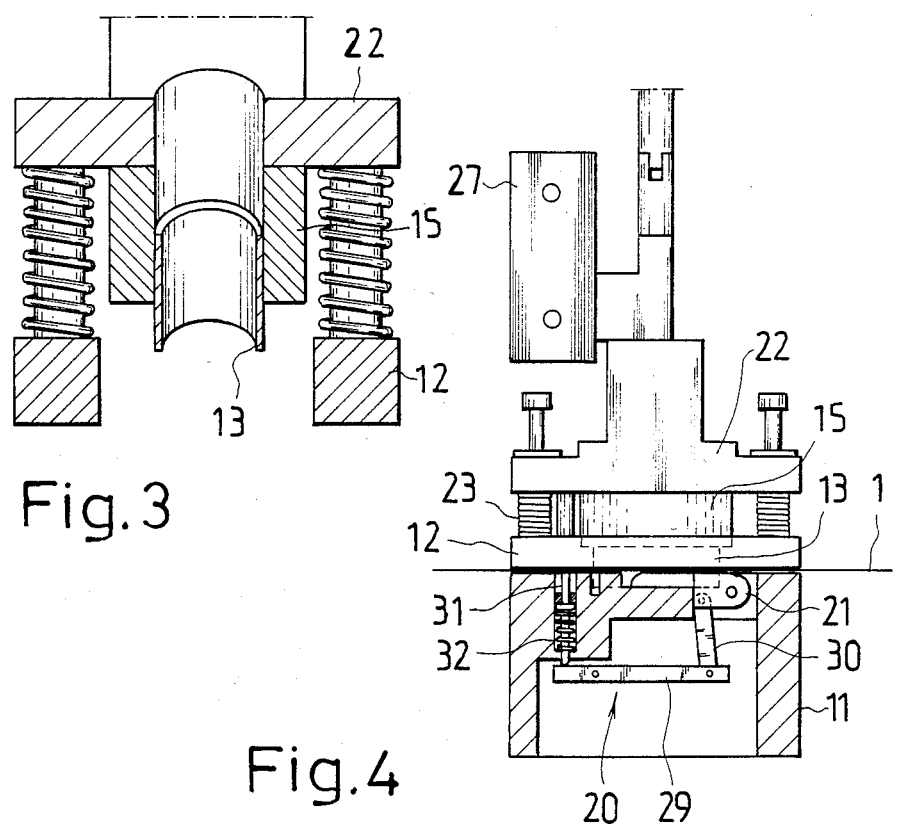
Fig. 3
Fig. 4

METHOD OF MEASURING TEAR RESISTANCE OF PAPER AND APPARATUS FOR APPLYING THE METHOD

BACKGROUND OF THE INVENTION

The present invention relates to a method of measuring the tear resistance of paper as well as to an apparatus for applying the method.

At present, the tear resistance of paper samples is determined in separate air-conditioned laboratory rooms. The actual determination is generally effected by means of a tear resistance measuring device operating on standardized pendulum principle. A sample is manually cut into precision measured packs of dimension sample blanks, comprising four sheets on top of each other and being manually fixed by means of clamping screws in a measuring device. The fixed pack of sample blanks is torn at precise length by means of potential energy of a pendulum. The effort required for tearing is determined as the reduction of potential energy possessed by said pendulum. Tear resistance can now be calculated on the basis of a given formula.

The present day methods and assemblies for carrying out tear resistance measurements involve drawbacks leading to inaccurate and deficient results in view of practical conditions. When today's measuring methods are employed, the sample blanks are cut out and fixed manually. During the treatment, the properties of a sample may change from original (e.g. moisture). Performing the measuring requires staff trained for the job and measurements should be effected in an airconditioned laboratory room. Furthermore, the measuring results always depend to some extent on a person doing the job. This drawback is due to the manner and ability characteristic of a person doing the measuring to cut out, fix and handle a sample blank as well as to the manner and ability to observe and read the analogous measuring results at the moment of measurement.

When the properties of paper are being tested, the aim is to apply the test results for the control of production processes or for watching the application properties. When using the available methods and devices, there is always a substantial time lapse between sampling and measuring events, during which the properties of a sample may alter and measuring results cannot be used immediately after the sampling. At present, the tear resistance is determined by tearing a pack of sample blanks comprising a plurality of sheets on top of each other. In the working conditions, however, it is essential to know the behavior of an individual sheet of paper which is why the available methods and devices are insufficient.

When using the available methods, a pack of sample blanks is torn by means of a pendulum and the effort required by tearing is determined as reduction of the potential energy of said pendulum. During the tear measuring, the strength of a force keeping up the tearing is not monitored, nor can the tearing rate be adjusted. Furthermore, a pendulum produces an increasing tearing force, the accurate strength of a force required for tearing being difficult to measure.

An object of the invention is to provide a method for determination of the tear resistance of paper in order to eliminate drawbacks of the available methods. A particular object of the invention is to provide a method utilized for testing a single layer paper in a manner that tearing rate can be adjusted. Another object of the invention is to provide a method, wherein paper is torn at a constant rate while continuously monitoring the level of tearing force. A still further object of the invention is to provide an apparatus for applying the method, the use of said apparatus eliminating some of the handling of a paper sample earlier necessary and said apparatus facilitating the immediate availability of measured results. An object of the invention is also to provide an apparatus for automatically handling, tearing and determining the tear resistance of paper.

The object of this invention is achieved by means of a method and apparatus substantially characterized by what has been set forth in the annexed claims.

SUMMARY OF THE INVENTION

According to the invention, a paper sample is provided with a tongue-shaped measuring blank whose one end is secured to the paper sample and said paper sample is torn by displacing the test blank and/or paper sample relative to each other in opposite directions and the tearing force is measured. A measuring blank can be displaced relative to a paper sample or a paper sample relative to a test blank. The method is used to determine the tear resistance properties of an individual sample blank and, since nearly all paper applications always involve the use of a single layer paper, the method according to the invention provides a determination of the tear resistance of sample paper corresponding to the working applications more accurately than the prior art methods. In addition, the product of the paper making process is a single layer sheet of paper and, thus, the method of this invention provides more accurate data on production processes than the prior art methods. The novel method speeds up the measuring decisively and it can be applied to effect the regulation of tear resistance by controlling the relative proportions of masses employed in a production process.

According to the invention, a test blank is preferably made by cutting a paper sample at a predetermined distance from each other two substantially parallel cut-outs as well as a cut-out connecting one end of the former. A paper sample is torn by affixing a test blank to a gripping means and by setting the gripping means in motion relative to the paper sample parallel to said cut-outs. Thus, the paper sample is torn by means of two shredders.

A paper sample is preferably torn by displacing the gripping means at a constant speed through the tearing movement. By means of the continuous control of a measuring event it is possible to determine the instantaneous value of a force keeping up the tearing as well as to determine the instantaneous tearing length during the entire tearing procedure. One of the factors revealed this way is the tearing resistance homogeneity of paper which is very important in view of consistent quality. In addition, the tearing rate can be varied when testing various paper grades.

According to the invention, a test blank is preferably secured to the gripping means in a manner that the angle between test blank and paper sample is circa 90°. In addition, the test blank is pulled so as to make its tearing direction substantially perpendicular to a paper sample. This way the tearing action is readily measurable and said tearing action does not alter the properties of paper.

An apparatus of the invention for applying the method is readily transportable and it can be operated in the immediate vicinity of a production or application process resulting in immediate availability of test results without any time lapse and the eventual readjustments can be made immediately. The apparatus comprises means required for cutting, tearing and measuring of paper and the operations proceed automatically, so a sample need not be handled during testing and the drawbacks due to such handling will be avoided.

BRIEF DESCRIPTION OF THE DRAWINGS

The invention will now be described in more detail with reference made to the accompanying drawing, in which FIG. 2 is a section along line II—II in FIG. 1, FIG. 3 is a section along line III—III in FIG. 1, FIG. 4 is a partially sectional view of a detail of the apparatus shown in FIG. 1 in cutting position.

DETAILED DESCRIPTION OF THE INVENTION

Figure 1:
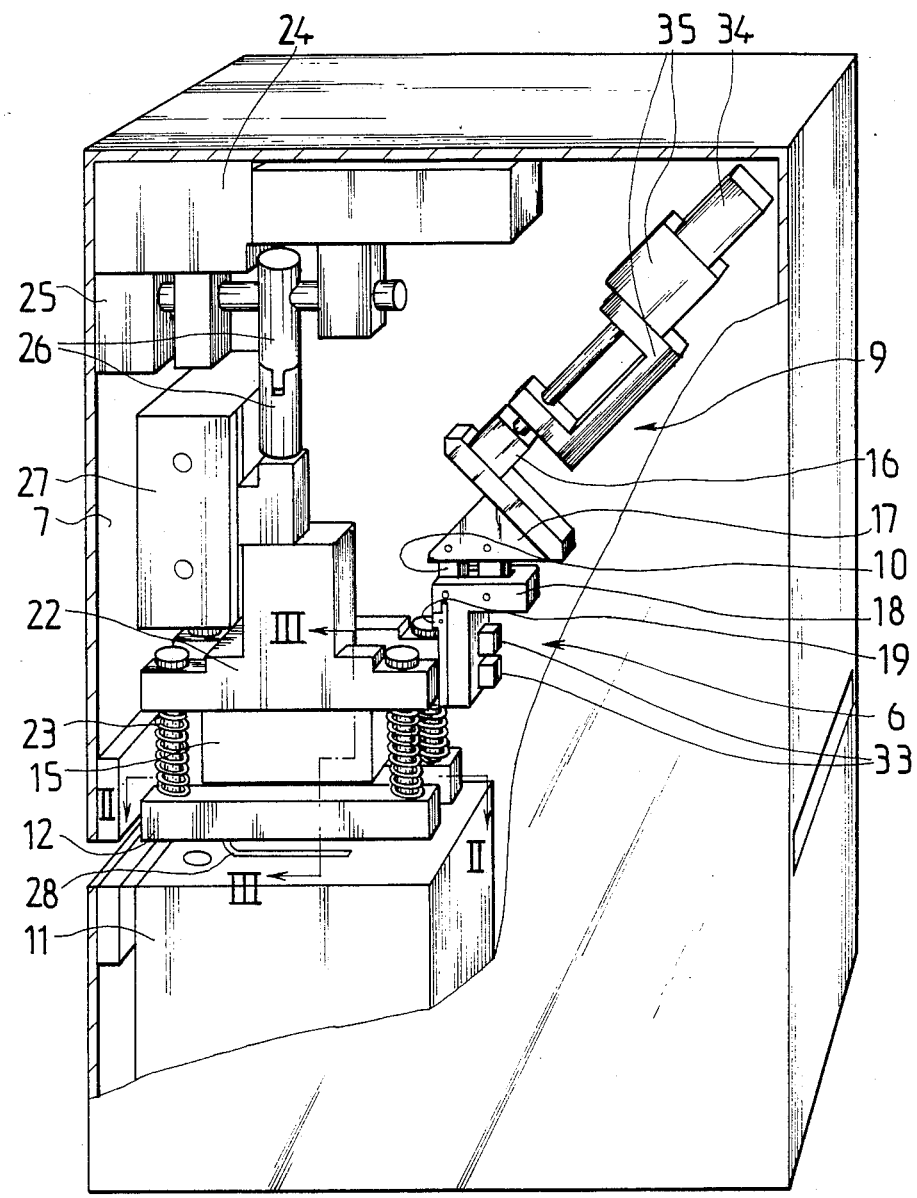
FIG. 1 shows one special embodiment of an apparatus of the invention partially cut away and viewed obliquely from the side.

The special embodiment of an apparatus of the invention shown in FIG. 1 comprises a body 7 housing the required equipment. The apparatus comprises a cutter device 8, comprised of a drive means 15 and tools 13, 14 mounted thereon. In the apparatus shown in the figures, said tools are made of a U-shaped cutter. Said cutter device 8 is affixed to a support member 22. Mounted on the support member is also a fastening means 12. The fastening means is constructed of two fastening brackets 12, mounted on either side of the cutter device and connected by way of spring screws 23 at both ends to support member 22. In their rest position, said fastening brackets are positioned to lie below the plane of said cutting tool. The apparatus is provided with a motor 24 for displacing the support member as well as a transmission gear 25 for transmission of power by way of link rods 26 to the support member. A guide 27 is secured to the body or housing and the support member is adapted to move under the control of said guide.

The apparatus comprises a base 11 fastened to the housing, said support member along with its fixed cutting and fastening means being displaceable relative to said base. The top face of said base is provided with a groove 28 whose configuration complies with that of the cutting tools. The base is provided with a turning gear 20, comprising a bar 29, a tappet 30 articulated to said bar, and a swivel head 21 linked to said tappet. The turning gear comprises a pin 31 which is displaceably fitted in a bore 32 opening into the plane of said base.

The apparatus is further provided with a gripping means 6, comprised of a main element 18 and a gripping jaw 19 movably linked to said main element. The gripping jaw is adapted to be urged against said main element for securing a test blank between main element and gripping jaw under the control of a drive means 33. The gripping means is fastened to the end 17 of the bracket 16 of a shifting means 9. Said shifting means 9 and its associated gripping means are displaceable by means of motor 34 and transmission gear 35. The shifting means is mounted on the gripping means by means of brackets 36. Said brackets are beam-like members with one end secured to the end 17 of the support or bracket of said shifting means and other ends to the main element 18 of said gripping means. One of the brackets is fitted with a measuring device 10 for the determination of tearing force.

Figure 5:
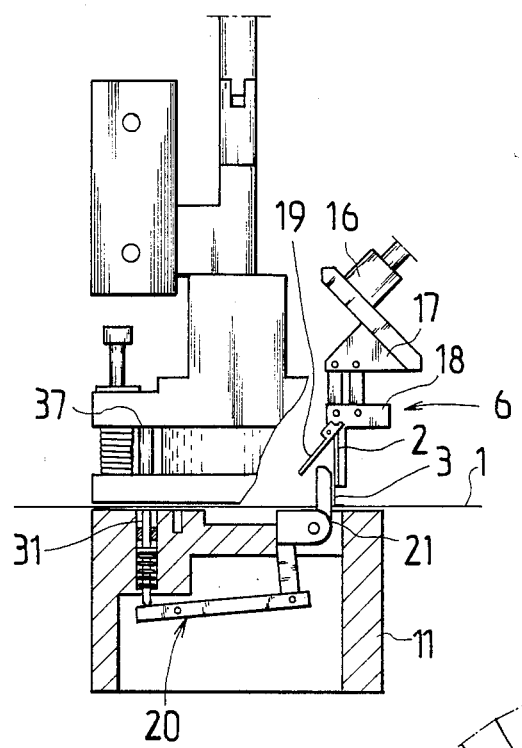
FIG. 5 shows a partially sectional detail of the apparatus of FIG. 1 in gripping position.

For measuring the tear resistance of paper, a sample of paper is introduced between said cutter device and the base of the apparatus. The paper sample 1 can be introduced into and shifted in the apparatus in a per se known manner by means of various transfer devices, not shown in the figures. The apparatus may also be installed to serve as one piece of equipment used for testing various properties of paper, in which case the conveyor of such assembly unit also serves as the conveyor of an apparatus of the invention. A paper sample may also be manually introduced into an apparatus of the invention. After a paper sample is inserted in the apparatus, said support member 22 is moved towards base 11. The support member, pushed by link rods 26, travels downwards in a groove located in guide 27. As the support member proceeds towards the base, said fastening brackets 12 press against the base fixing a paper sample between the base and the fastening brackets. As the downward movement of support member is continued, springs 23 are compressed and fastening brackets fix the piece of paper in position. According to FIG. 4, the support member is urged downwards until the dash-line designated cutting tools 13 has cut out of paper sample 1 a tongue-shaped test blank 2 when pushed into a groove 28 made in the base and having the same shape as said cutting tools. A rod 37 shown in FIGS. 2 and 5 is fastened to the support member and travels downwards therealong and pierces the paper sample, shifting said pin 31 downwards. Thus, according to FIG. 5, pin 31 acts on one end of bar 29, the other end of said bar rising upwards to displace tappet 30 which turns a swivel head linked to the base, so that said swivel head swings the cut-out test blank 2 away from the plane of a paper sample towards gripping means 6. The gripping means has been brought into the vicinity of a sample and the gripping jaw is in open position, so the swivel head swings the test blank in a manner that the cut-out end of said test blank finds its way between the main element 18 and the gripping jaw of said gripping means. The gripping jaw is pressed against the main element, the test blank being caught between said gripping jaw and main element.

Figure 6:
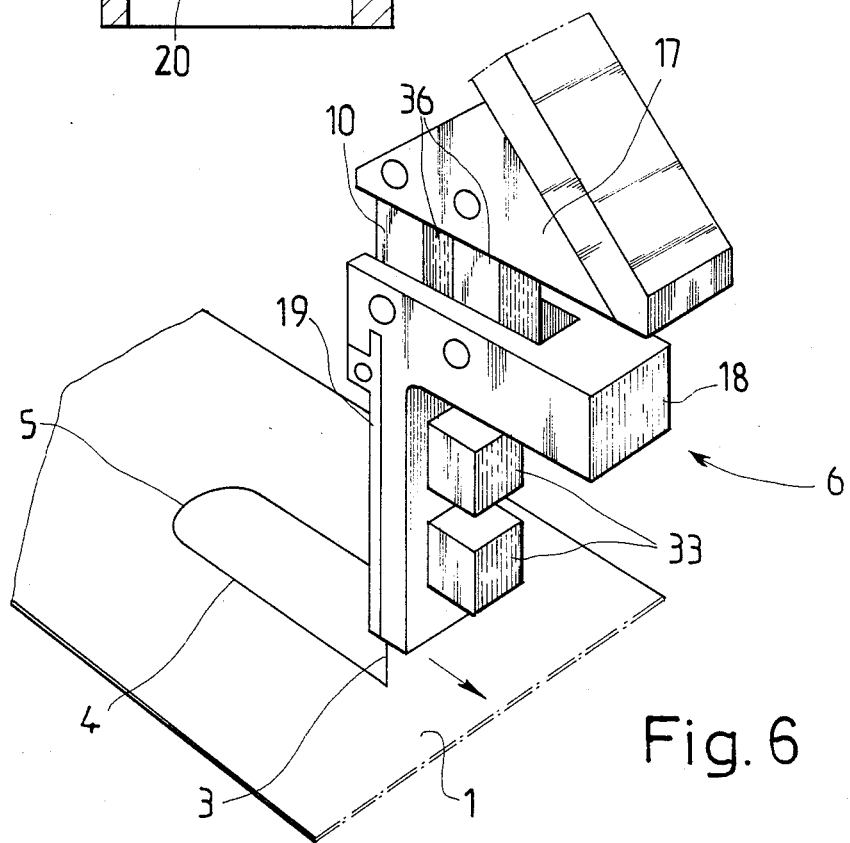
FIG. 6 illustrates tearing of a paper sample by means of the apparatus shown in FIG. 1.

According to FIG. 6, the test blank is secured to the gripping means so that the angle between test blank and paper sample will be circa 90°. The gripping means is set in motion by displacing the shifting means at a constant speed in a constant direction, preferably at the angle of 45°, relative to a paper sample. Thus, the tearing direction of a test blank will be substantially perpendicular relative to said paper sample since the angle between gripping means and paper sample remains at circa 90° throughout the tearing process. A test blank is pulled parallel to cut-outs 4, the sample being torn at the end 3 of said test blank substantially parallel to the cut-outs. The tearing procedure is monitored by measuring the rate and force of tearing by means of a measuring device mounted on bracket 36. The measured results are displayed in a per se known manner by means of some appropriate output equipment.

The invention has been explained above by referring to one particular apparatus for applying the method of the present invention but it should be appreciated that the invention is not limited to this apparatus alone but other embodiments are also possible within the invention set out in the annexed claims. The shape of tools used in the apparatus may vary and tool 13 and tool 14 can be adapted to work separately and with diversified timing. The shifting means can also be displaced in some other direction than at the angle of 45° relative to a paper sample. In some embodiments, the angle between paper sample and gripping means may be smaller or greater than 90°.

We claim:

1. A method of measuring tear resistance of paper, characterized in that a paper sample (1) is provided with a tongue-shaped test blank (2), whose one end (3) is secured to the paper sample, the latter being torn by pulling the test blank and/or paper sample relative to each other in different directions and tearing force is measured.

2. A method as set forth in claim 1, characterized in that said test blank (2) is produced by cutting into the paper sample at a determined distance from each other two substantially parallel cut-outs (4) and a cut-out (5) connecting one of the ends thereof.

3. A method as set forth in claim 2, characterized in that the paper sample is torn by fastening test blank (2) to a gripping means (6) and by setting the gripping means in motion relative to the paper sample parallel to cut-outs (4).

4. A method as set forth in claim 3, characterized in that said paper sample is torn by displacing the gripping means at a constant speed throughout the tearing motion.

5. A method as set forth in claim 3 or 4, characterized in that said test blank is fastened to the gripping means in such a manner that the angle between test blank and paper sample is circa 90°.

6. A method as set forth in claim 5, characterized in that said test blank is pulled in a manner that the tearing direction of the test blank is substantially perpendicular to said paper sample.

7. An apparatus for measuring tear resistance of paper characterized in that said apparatus comprises a housing (7), a cutter device (8) fitted inside the housing and displaceable relative to a paper sample (1) inserted into the apparatus, said cutter device being adapted to cut out of the paper sample a tongue-shaped test blank (2) whose one end (3) is secured to the paper sample, a shifting means (9) mounted on the housing, a gripping means (6) linked to said shifting means, said gripping means being adapted to catch the test blank and said shifting means being adapted to displace the gripping means relative the paper sample, as well as a measuring device (10) for measuring the tearing force.

8. An apparatus as set forth in claim 7, characterized in that said apparatus comprises a base (11) secured to the housing and a fastening means (12) displaceable relative to said housing and said base, said fastening means being adapted to fix a paper sample introduced between the base and fastening means by pressing it against said base (11).

9. An apparatus as set forth in claim 8, characterized in that said base comprises a turning gear (20) whose swivel head (21) is mounted at the test blank and adapted to swing the cut-out end of said test blank away from the plane of a paper sample towards the gripping means.

10. An apparatus as set forth in claim 7 or 8, characterized in that said cutter device (8) comprises two parallel, spaced-apart tools (13) and a tool (14), the latter being adapted to cut out of the paper sample a cut-out connecting those made with the former tools.

11. An apparatus as set forth in claim 10, characterized in that said cutter device comprises a drive means (15) to which tools (13, 14) are mounted and which is adapted to move said tools towards base (11) and paper sample (1) for cutting out said test blank.

12. An apparatus as set forth in claim 7, characterized in that said shifting means (9) comprises a bracket member (16), which is adapted to be displaced relative to the paper sample and on whose end (17) are mounted gripping means (6) and measuring device (10).

13. An apparatus as set forth in claim 1, characterized in that said gripping means (6) comprises a main element (18), linked to bracket member (16) of shifting means (9), and a gripping jaw (19) displaceably linked to the main element, said gripping jaw being adapted to be pressed against the main element (18) for fastening the test blank between the main element and the gripping jaw.

* * * * *